United States Patent [19]
Durant et al.

[11] Patent Number: 5,489,709
[45] Date of Patent: Feb. 6, 1996

[54] PREPARATION OF SUBSTITUTED GUANIDINES

[75] Inventors: Graham J. Durant; Sharad S. Magar, both of Toledo, Ohio

[73] Assignees: Cambridge Neuroscience, Inc.; University of Toledo

[21] Appl. No.: 192,990

[22] Filed: Feb. 8, 1994

Related U.S. Application Data

[62] Division of Ser. No. 854,496, Mar. 20, 1992, Pat. No. 5,298,657.

[51] Int. Cl.$^6$ ............................................. C07C 277/02
[52] U.S. Cl. ...................... 564/238; 564/237; 564/239; 546/134; 546/143; 546/306
[58] Field of Search ......................... 564/238, 239

[56] References Cited

U.S. PATENT DOCUMENTS

| | | | |
|---|---|---|---|
| 1,756,315 | 4/1930 | ter Horst | 564/238 |
| 2,258,321 | 10/1941 | Ericks | 564/239 |
| 2,289,541 | 7/1942 | Ericks et al. | 564/239 |
| 3,914,306 | 10/1975 | Douglas et al. | 564/239 |
| 4,051,256 | 9/1977 | Swallow | 424/304 |
| 4,709,094 | 11/1987 | Weber et al. | 564/238 |

FOREIGN PATENT DOCUMENTS

| | | |
|---|---|---|
| 2215556 | 9/1987 | Japan . |
| WO91/12797 | 9/1991 | WIPO .......................... A61K 31/155 |
| WO92/00273 | 1/1992 | WIPO .......................... C07C 279/18 |

OTHER PUBLICATIONS

Cooper et al. "N-Phenylbenzamidine" Organic Synthesis, Coll. vol. IV, 769–771 (1963).

Geluk et al. "Synthesis and Antiviral Properties of 1-Adamantylguanidine. A Modified Method for Preparing t-Alkylguanidines", Journal of Medical Chemistry 12:711–715, 1969.

Safir et al. "Experimental Chemotherapy of Trypanosomiasis. II. The Preparation of Compounds Related to p-Phenylenediguanidine", Journal of Organic Chemistry 924–932, 1948.

Oxley et al. "Amidines. Part VII. Preparation of Amidines from Cyanides, Aluminium Chloride, and Ammonia or Amines", Journal of Chemical Society 1110–1116, 1947.

*Primary Examiner*—Peter O'Sullivan
*Attorney, Agent, or Firm*—Fish & Richardson

[57] ABSTRACT

A process for the preparation of a substituted guanidine by reacting a substituted cyanamide with ammonia or a substituted amine in the presence of a Lewis acid catalyst. Also disclosed is a process for the preparation of a tri-substituted guanidine by reacting a mono-substituted cyanamide with a di-substituted amine.

2 Claims, No Drawings

PREPARATION OF SUBSTITUTED GUANIDINES

This a divisional of application Ser. No. 07/854,496, filed Mar. 20, 1992, now U.S. Pat. No. 5,298,657.

FIELD OF THE INVENTION

The invention relates to chemical synthetic methods for preparing various substituted guanidines from cyanamide derivatives and ammonia or amine derivatives.

BACKGROUND OF THE INVENTION

Substituted guanidines have a wide field of use. For example, 1,3-diphenyl guanidines and like substituted guanidines are accelerators for the vulcanization of rubbers. Thus, such guanidine derivatives, when radiolabeled, can be incorporated into a vulcanized rubber object (e.g., a tire tread) and rate of loss of rubber therefrom by water can be monitored by rate of loss of radioactivity. As another example, 1,3-di-(o-tolyl) guanidine may act in an agonistic, antagonistic or inverse agonistic manner in relation to the prototypical sigma benzomorphans and therefore can affect pupil size and heart rate in a direction parallel or opposite that caused by benzomorphans which can be determined by standard tests in laboratory animals. See U.S. Pat. No. 4,709,094, which is incorporated herein by reference.

Similarly, certain tri- and tetra-substituted guanidines, e.g., N-(1-naphthyl)-N'-(3-ethylphenyl)-N'-methyl guanidine, also exhibit exceptionally low binding to the sigma brain receptor. Such compounds can thus be used for treating diseases of the nervous system in which the pathophysiology of the diseases involves excessive excitation of nerve cells by agonists of the glutamate/N-methyl-D-Aspartate (NMDA) receptor. See U.S. patent application Ser. No. 07/663,134, also incorporated herein by reference.

The synthesis of substituted guanidines by reaction of ammonia or amine derivatives with cyanamide derivatives is a well-known reaction. Symmetrical or unsymmetrical N,N'-disubstituted guanidines can be conveniently made by reaction of an appropriate amine with an appropriate cyanamide either by fusion or in a suitable boiling solvent such as chlorobenzene. Safir, S. R. et al. J. Org. Chem. 13: 924 (1948); Gulek, H. W. et al. J. Med. Chem. 12:712 (1969). For example, see Reaction (I) set forth below in which each $R^1$ and $R^2$ is aryl or alkyl.

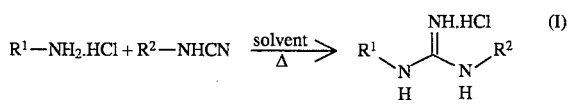
(I)

However, preparation of tri- or tetra-substituted guanidines using the same reaction is limited by the lower nucleophilicity of the secondary amines or inversely lower electrophilicity of the substituted cyanamides. Indeed, the reaction of a secondary amine and disubstituted cyanamide is a very low yield synthesis (0–20%) of substituted guanidine even under forcing conditions involving fusion at temperatures as high as 200° C., coupled with difficult product isolation and purification. Thus, it is very difficult and impractical to use Reaction (I) for large scale synthesis of unsymmetrical tetra-substituted guanidines.

Also, the reaction of a monosubstituted amine and a disubstituted cyanamide to produce a trisubstituted cyanamide can be a very low yield synthesis, coupled with difficult product isolation and purification. For example, the yield of N-(1-naphthyl)-N'-(3-ethylphenyl)-N'-methyl guanidine from 1-naphthylamine and N-methyl, N-(3-ethylphenyl) cyanamide is as low as 17%. The reason for the poor yields can be attributed to the steric hindrance offered by the methyl group of N-methyl, N-(3-ethylphenyl) cyanamide to the approach of the nucleophilic amine.

SUMMARY OF THE INVENTION

In general, one aspect of the present invention features enhancement of the electrophilicity and reactivity of the disubstituted cyanamide by complex formation with a Lewis acid catalyst which makes the carbon center of cyanamide more active towards nucleophilic amines in Reaction (I).

Thus, within the invention is a process for the preparation of a substituted guanidine which comprises reacting a substituted cyanamide with ammonia or a substituted amine in the presence of a Lewis acid catalyst.

Preferably, in this catalytic process the substituted cyanamide

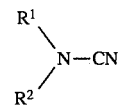

and the ammonia or substituted amine is $R^3$-NH-$R^4$ in which each $R^1$ and $R^2$ independently is a $C_1$-$C_8$ alkyl group, a $C_3$-$C_{12}$ cycloalkyl group, a $C_2$-$C_8$ alkenyl group, a $C_2$-$C_8$ alkynyl group, a $C_6$-$C_{14}$ aryl group, a $C_6$-$C_{14}$ aryl group with an aromatic moiety substituted by OH, halogen, $C_1$-$C_5$ alkoxy, azido, amino, cyano, or nitro, a $C_{11}$-$C_{18}$ aralkyl or alkaryl group, a $C_{11}$-$C_{18}$ aralkyl or alkaryl group with an aromatic moiety substituted by OH, halogen, $C_1$-$C_5$ alkoxy, azido, amino, cyano, or nitro, a $C_4$-$C_{18}$ heteroaromatic group, or a $C_4$-$C_{18}$ heteroaromatic group with an aromatic moiety attached thereto, form a $C_4$-$C_{18}$ heterocyclic group; and each $R^3$ and $R^4$ independently is H, a $C_1$-$C_8$ alkyl group, a $C_3$-$C_{12}$ cycloalkyl group, a $C_{2C8}$ alkenyl group, a $C_2$-$C_8$ alkynyl group, a $C_6$-$C_{14}$ aryl group, a $C_6$-$C_{14}$ aryl group with an aromatic moiety substituted by OH, halogen, $C_1$-$C_5$ alkoxy, azido, amino, cyano, or nitro, a $C_{11}$-$C_{18}$ aralkyl or alkaryl group, a $C_{11}$-$C_{18}$ aralkyl or alkaryl group with an aromatic moiety substituted by OH, halogen, $C_1$-$C_5$ alkoxy, azido, amino, cyano, or nitro, a $C_4$-$C_{18}$ heteroaromatic group, or a $C_4$-$C_{18}$ heteroaromatic group with an aromatic moiety substituted by OH, halogen, $C_1$-$C_5$ alkoxy, azido, amino, cyano, or nitro or $R^3$ and $R^4$, together with the nitrogen attached thereto, form a $C_4$-$C_{18}$ heterocyclic group. It is further desired that the $R^3$NH-$R^4$ be mono- or di-substituted.

A particularly preferred embodiment of the process is one in which $R^1$ is a $C_1$-$C_8$ alkyl group, $R^2$ is a $C_6$-$C_{14}$ aryl, a $C_{11}$-$C_{18}$ aralkyl group, or a $C_4$-$C_{18}$ heteroaromatic group, $R^3$ is H or a $C_1$-$C_8$ alkyl group, and $R^4$ is a $C_6$-$C_{14}$ aryl group, a $C_{11}$-$C_{18}$ aralkyl group, or a $C_4$-$C_{18}$ heteroaromatic group; it is preferable that $R^1$ be methyl, $R^2$ be benzyl, 3-ethyl-phenyl, 8-coumarinyl, or 1-naphthyl, $R^3$ be H or methyl, and $R_4$ be benzyl, 3-ethyl-phenyl, 8-coumarinyl, 1-naphthyl, 2-pyridyl, 5-quinolinyl, 8-quinolinyl, or 5-isoquinolinyl. Other preferred embodiments include the process in which $R^1$ is methyl, $R^2$ is 3-ethyl-phenyl, $R^3$ is methyl, and $R^4$ is 1-naphthyl, and the process in which R1 is methyl, R2 is 3-ethyl-phenyl, R3 is H, and R4 is 1-naphthyl.

Another aspect of the present invention features avoidance or diminishment of the steric hindrance involved in the synthesis of a trisubstituted guanidine by reaction of substituted amines with substituted cyanamides.

Another aspect of the present invention features avoidance or diminishment of the steric hindrance involved in the synthesis of a tri-substituted guanidine by reaction of substituted amines with substituted cyanamides. More specifically, also within the invention is a process for the preparation of a tri-substituted guanidine which comprises reacting a mono-substituted cyanamide with a di-substituted amine.

In a preferred embodiment of this non-catalytic process, the mono-substituted cyanamide is

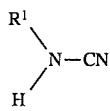

and the di-substituted amine is $R^2$-NH—$R^3$ in which $R^1$ is a $C_1$–$C_8$ alkyl group, a $C_3$–$C_{12}$ cycloalkyl group, a $C_2$–$C_8$ alkenyl group, a $C_2$–$C_8$ alkynyl group, a $C_6$–$C_{14}$ aryl group, a $C_6$–$C_{14}$ aryl group with an aromatic moiety substituted by OH, halogen, $C_1$–$C_5$ alkoxy, azido, amino, cyano, or nitro, a $C_{11}$–$C_{18}$ aralkyl or alkaryl group, a $C_{11}$–$C_{18}$ aralkyl or alkaryl group with an aromatic moiety substituted by OH, halogen, $C_1$–$C_5$ alkoxy, azido, amino, cyano, or nitro, a $C_4$–$C_{18}$ heteroaromatic group, or a $C_4$–$C_{18}$ heteroaromatic group with an aromatic moiety substituted by OH, halogen, $C_1$–$C_5$ alkoxy, azido, amino, cyano, or nitro; and each $R^2$ and $R^3$ independently is a $C_1$–$C_8$ alkyl group, a $C_3$–$C_{12}$ cycloalkyl group, a $C_2$–$C_8$ alkenyl group, a $C_2$–$C_8$ alkynyl group, a $C_6$–$C_{14}$ aryl group, a $C_6$–$C_{14}$ aryl group with an aromatic moiety substituted by OH, halogen, $C_1$–$C_5$ alkoxy, azido, amino, cyano, or nitro, a $C_{11}$–$C_{18}$ aralkyl or alkaryl group, a $C_{11}$–$C_{18}$ aralkyl or alkaryl group with an aromatic moiety substituted by OH, halogen, $C_1$–$C_5$ alkoxy, azido, amino, cyano, or nitro, a $C_4$–$C_{18}$ heteroaromatic group, or a $C_4$–$C_{18}$ heteroaromatic group with an aromatic moiety substituted by cyano or nitro, a $C_{11}$–$C_{18}$ aralkyl or alkaryl group, a $C_{11}$–$C_{18}$ aralkyl or alkaryl group with an aromatic moiety substituted by OH, halogen, $C_1$–$C_5$ alkoxy, azido, amino, cyano, or nitro, a $C_4$–$C_{18}$ heteroaromatic group, or a $C_4$–$C_{18}$ heteroaromatic group with an aromatic moiety substituted by OH, halogen, $C_1$–$C_5$ alkoxy, azido, amino, cyano, or nitro, and each $R^2$ and $R^3$ independently is a $C_1$–$C_8$ alkyl group, a $C_3$–$C_{12}$ cycloalkyl group, a $C_2$–$C_8$ alkenyl group, a $C_2$–$C_8$ alkynyl group, a $C_6$–$C_{14}$ aryl group, a $C_6$–$C_{14}$ aryl group with an aromatic moiety substituted by OH, halogen, $C_1$–$C_5$ alkoxy, azido, amino, cyano, or nitro, a $C_{11}$–$C_{18}$ aralkyl or alkaryl group, or a $C_{11}$–$C_{18}$ aralkyl or alkaryl group with an aromatic moiety substituted by OH, halogen, $C_1$–$C_5$ alkoxy, azido, amino, cyano, or nitro.

A particularly preferred embodiment of this non-catalytic process is one in which the monosubstituted cyanamide is N-(1-naphthyl) cyanamide and the disubstituted amine is N-methyl-3-ethyl aniline.

It is preferred that the above-described synthetic processes, both catalytic and non-catalytic, be performed by refluxing in a boiling solvent, such as toluene or chlorobenzene. Also note that the ammonia or substituted amine can be either in its salt form or free base. Salt form, e.g., hydrochloride, is preferred.

The term "Lewis acid catalyst" refers to an acid that is an electron-pair acceptor according to the Lewis definition. Commonly used Lewis acid catalysts include boron trichloride $BCl_3$; aluminum chloride $AlCl_3$; titanium tetrachloride $TiCl_4$; boron trifluoride $BF_3$; tin tetrachloride $SnCl_4$; and zinc dichloride $ZnCl_2$. Other examples are boron tribromide $BBr_3$, aluminum tribromide $AlBr_3$, ferric chloride $FeCl_3$, gallium trichloride $GaCl_3$, antimony tribromide $SbBr_3$, antimony pentachloride $SbCl_5$, antimony pentafluoride $SbF_5$, mercuric chloride $HgCl_2$, triphenyl-10-chloride, triphenyl aluminum, and triphenyl borate. $AlCl_3$ is most preferred. See Organic Synthesis, Coll. Vol. IV, pp. 769–771 and Oxley, P. et al. J. Chem. Soc., London, pp. 1110–1116, Part II (1947), both of which are incorporated herein by reference.

Typical alkyl groups are, for example, methyl, ethyl, propyl, isopropyl, butyl, isobutyl, tert-butyl, hexyl, heptyl and octyl.

Typical cycloalkyl groups are cyclopropyl, cyclopentyl, cyclohexyl, cycloheptyl, 1,4-methylenecyclohexyl, adamantyl, noradamantyl, norbornyl, isobornyl, cyclopentylmethyl, cyclohexylmethyl, 1- or 2-cyclohexylethyl and 1-, 2- or 3-cyclohexylpropyl.

Typically, alkenyl groups include allyl, 2-butenyl, 2-pentenyl and 2-hexenyl groups.

Typical alkynyl groups are 2-butynyl, 2-pentynyl and 2-hexynyl.

Typically, aryl, alkaryl and aralkyl groups and substitution groups thereof include benzyl, phenyl, 1-naphthyl, 2-naphthyl, biphenyl, phenanthryl, 3-acenaphthenyl, 5-acenaphthenyl, anthracyl, 1- and 2-phenylethyl, 1-, 2-, or 3-phenylpropyl, o-, m-, or p-tolyl, m,m'-dimethyl-phenyl, o-, m-, or p-ethylphenyl, m,m'-diethylphenyl, m-methyl-m'-ethylphenyl, o-propylphenyl, and o-isopropylphenyl, o or m-iodophenyl, o, m or p- isopropyl phenyl, o or m-methorylphenyl, o or m-trifluoromethyl phenyl, 4-fluoro-3-ethyl phenyl, 3-nitrophenyl, 4-fluoro-3-nitrophenyl, 3-azido phenyl, 4-bromo-3-ethyl phenyl, 6-methoxy-3-ethyl phenyl, 4-fluoro-3-methyl phenyl, 4-bromo-3methyl phenyl, 4-fluoro-3-trifluoromethyl phenyl, 4-fluoro-3-ethyl phenyl, 4-fluoronaphthyl, 7-fluoronaphthyl, 4-methoxy naphthyl, 4-hydroxy naphthyl and 2-fluoronaphthyl.

Typically, heteroaromatic groups and substitution groups thereof include pyridyl, pyridazinyl, pyrazinyl, pyrimidyl, furyl, pyrrolyl, thienyl, thiazolyl, oxazolyl, imidazolyl, indolyl, 8-coumarinyl, 5-quinolinyl, 8-quinolinyl, 5-isoquinolinyl, benzofuranyl, benzthiazolyl groups, piperidinyl, piperazinyl, 4-phenyl piperidinyl, phenyl piperizinyl and their substituted derivatives.

Typical substituents on the aromatic ring of the above-mentioned aryl, alkaryl, aralkyl and heteroaromatic groups include OH, halogen (e.g., I, Br, Cl, or F), alkoxy (e.g., methoxy or ethoxy), amino, cyano, azido and nitro.

The heterocyclic groups recited herein refer specifically to nitrogen-containing ring structures. In addition to some of the heteroaromatic groups listed above (e.g., indolyl), they typically include pyrrolidyl, piperidyl, 1,2,3,4-tetrahydroquinolinyl, and carbazolyl groups.

The above-described processes, both catalytic and non-catalytic, cause a dramatic increase in yield and facilitate product isolation and purification. In particular, the catalytic synthetic process involves use of rather inexpensive catalysts and is thus commercially attractive. More importantly, the method of the invention enables one to synthesize tri- and tetra-substituted guanidines employing otherwise inactive heteroaromatic amines.

Other features and advantages of the invention will be apparent from the following detailed description, and from the claims.

DESCRIPTION OF THE PREFERRED EMBODIMENTS

A Catalytic Process for Preparing Substituted Guanidines

The catalytic method for preparing tri- and tetra-substituted guanidines is represented in the following scheme:

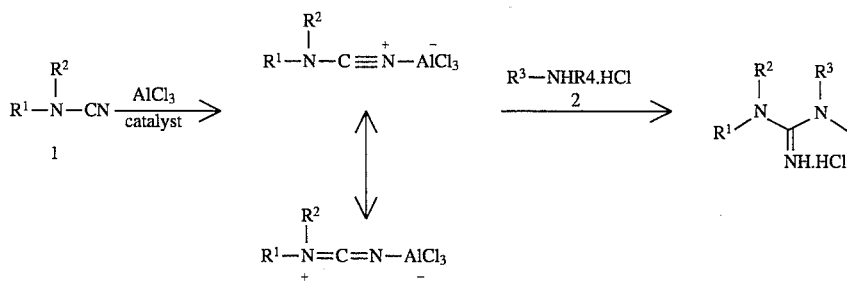

In Reaction (II), each $R^1$ and $R^2$ independently is alkyl, cycloalkyl, alkenyl, alkynyl, aryl, aralkyl or alkaryl, or heteroaromatic, and each $R^3$ and $R^4$ independently is H, alkyl, cycloalkyl, alkenyl, alkynyl, aryl, aralkyl or alkaryl, or heteroaromatic group.

Preferably, the cyanamide derivative 1 and the ammonia/amine derivative 2 (as a hydrochloride salt) are employed in the ratio of 0.9 mole equivalent of base per cyanamide group, and one mole equivalent of aluminum chloride ($AlCl_3$) is added to the mixture. A convenient method for separation of the desired guanidine hydrochloride corresponding amine by treatment with cyanogen bromide (BrCN) in dry ethereal solution and subsequent alkylation with alkyl halide/sodium hydride in dry tetrahydrofuran (THF) as shown in the following reaction:

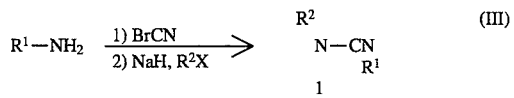

In Reaction (III), X stands for halogen.

The amine hydrochloride 2 can be prepared from commercially available amines by treatment with excess of anhydrous HCl in ether.

Provided below is a general procedure for the synthesis of di- or tri-substituted guanidines in the presence of a Lewis acid catalyst. To a stirred solution of the appropriate amine hydrochloride (9 mmol) and N-disubstituted cyanamide (10 mmol) in 10–15 ml chlorobenzene under nitrogen at room temperature is carefully added a total of 10 mmol anhydrous aluminum chloride over a period of 0.5 hr. A water cooled reflux condenser is then attached and the mixture is heated to reflux with vigorous stirring for 20–24 hrs. The contents are cooled to room temperature, diluted with approximately 20 ml absolute ethanol and the resulting solution is then concentrated in vacuo. The concentrated product mixture is chromatographed on a flash column (silica gel: 60–200 mesh, 50× w/w) by gradient elution with 5–25% MeOH in ethyl acetate. Analytically pure product is obtained by taking the chromatographed material in hot ethanol, stirring it with decolorizing charcoal (0.5 hr) and then filtering through Celite, followed by concentration and recrystallization from ethanol/ether or ethanol/ethyl acetate.

The syntheses of various tri- and tetra-substituted guanidines by the above-described procedure are summarized in Table 1, with detailed analytical data set forth in Examples 1–7, respectively. Note that the yields of guanidines reported in Table 1 are not necessarily the highest obtainable, i.e. not optimized, since the systematic examination of the effect of reaction conditions on the yield of guanidine was made only in a few cases. In Examples 8 and 9, a modified process was used. Code names of the substituted guanidines prepared are provided in both Table 1 and Examples 1–8.

A Non-catalytic Process for Preparing Substituted Guanidines

As discussed above, the reaction of a monosubstituted amine and a disubstituted cyanamide to produce a trisubstituted cyanamide can be a very low yield synthesis due to the steric hindrance from a substituent of the cyanamide reactant. Our research efforts in this area have indicated that the reaction of a monosubstituted cyanamide and a disubstituted amine hydrochloride results in a much higher yield, as compared to that between a

TABLE I

| Example | Starting Amine | Starting Cyanamide | Product | M. P. | % yield |
|---|---|---|---|---|---|
| 1 | naphthalen-1-yl-NH₂ | NC—N(Me)—(3-ethylphenyl) | CDD-2515A | 225° C. | 80% |

TABLE I-continued

| Example | Starting Amine | Starting Cyanamide | Product | M. P. | % yield |
|---|---|---|---|---|---|
| 2 | H-N(Me)-C6H4-Et | 1-naphthyl-N(Me)-CN | CDD-2516A | 128° C. | 74% |
| 3 | 1-naphthyl-NH2 | NC-N(Me)-C6H4-Et | CDD-2517A | 145° C. (dec) | 31% |
| 4 | 5-isoquinolinyl-NH2 | NC-N(Me)-C6H4-Et | CDD-2518A | 220° C. | 33% |
| 5 | 2-aminopyridine | 1-naphthyl-N(Me)-CN | CDD-2519A | 179° C. | 74% |
| 6 | 1-naphthyl-NH2 | NC-N(Me)-CH2-C6H5 | CDD-2520A | 176° C. | 55% |
| 7 | H-N(Me)-CH2-C6H5 | NC-N(Me)-C6H4-Et | CDD-2521A | 180° C. (dec) | 41% | monosubstituted amine hydrochloride and a disubstituted cyanamide, since in the former mode the nucleophilic secondary amine can easily approach the relatively unhindered secondary cyanamide.

This "reverse" reaction pathway offers considerable improvement over previously utilized methods not only in terms of yield, but also as regards to the ease of isolation and purification, since complete conversion to a single desired product eliminates the need for separation of the unreacted starting materials from the product.

Examples 10 demonstrates that reaction of 1-naphthyl cyanamide with N-methyl-3-ethyl aniline hydrochloride in chlorobenzene affords a near quantitative yield of CDD-2515A (81% yield after purification). Examples 11–15 show how guanidine derivatives with a halophenyl or alkoxyphenyl substituent can be prepared following a protocol similar to that set forth in Example 10.

Note that the non-catalytic process for preparing substituted guanidines from various reactants as shown in Examples 11–15 or analogs or homologs thereof is also within the invention. For example, the substituent of the mono-substituted cyanamide can be a $C_6$–$C_{18}$ aromatic group, and one substituent of the di-substituted amine can be a $C_1$–$C_5$ alkyl group and the other can be a $C_6$–$C_{12}$ aromatic group substituted by a halogen or by a $C_1$–$C_5$ alkoxy group.

Without further elaboration, it is believed that one skilled in the art can, using the preceding description, utilize the present invention to its fullest extent. The following specific embodiments are, therefore, to be construed as merely illustrative, and not limitative of the remainder of the disclosure in any way whatsoever.

EXAMPLE 1

Synthesis of N-(1-naphthyl)-N'-(3-ethylphenyl)-N'-methyl guanidine.HCl (CDD-2515A)

N-(1-naphthyl)-N'-(3-ethylphenyl)-N'-methyl guanidine.HCl was prepared from N-(1-naphthyl) amine.HCl and N-methyl, N-(3-ethylphenyl) cyanamide following the general catalytic process described above. Analytical data for the guanidine hydrochloride product are as follows:

Recrystallized from absolute ethanol/ethyl acetate; white solid: m.p. 225° C.; TLC $R_f$=0.2 [solvent MeOH:EtOAc 1:4]; $^1$H NMR (300 MHz, CD$_3$OD) δ7.96–8.00 (m, 3, Ar—H), 7.31–7.67(m, 8, Ar—H); 3.56(s, 3, N—CH$_3$), 2.70–2.77 (q, J=7.5 Hz, 2, CH$_2$, 1.25–1.30 (t, J=7.5 Hz, 3, CH$_3$); MS (El): m/e 303 (M$^+$ for free base); Anal. (C$_{20}$H$_{21}$N$_3$.HCl) Calcd (%): C 70.68, H 6.53, N 12.36. Found (%): C 70.41, H 6.40, N 12.23.

EXAMPLE 2

Synthesis of N-(1-naphthyl)-N'-(3-ethylphenyl)-N',-N-dimethyl guanidine.HCl (CDD-2516A)

N-(1-naphthyl)-N'-(3 -ethylphenyl)-N', N-dimethyl guanidine.HCl was prepared from N-methyl, N-(3-ethylphenyl) amine.HCl and N-methyl, N-(1-naphthyl) cyanamide following the general catalytic process described above. Analytical data for the guanidine hydrochloride product are as follows:

Recrystallized from absolute ethanol/ether; white solid: m.p. 128° C.; $^1$H NMR (300 MHz, CD$_3$OD) δ7.11–8.15 (m, 11, Ar—H), 3.57 (s, 3, N'—CH$_3$), 3.40 (s, 3, N—CH$_3$), 2.89 (br s, 1, NH), 2.61–2.68 (q, J=7.5 Hz, 2, CH$_2$), 1.19–1.24 (t, J=7.5 Hz, 3, CH$_3$); MS (El); m/e 317 (M$^+$for free base); Anal. (C$_{21}$H$_{23}$N$_3$. HCl) Calcd (%): C 71.27, H 6.84, N 11.87. Found (%): C 71.42, H 6 669 N 12 00.

EXAMPLE 3

Synthesis of N-(8-quinolinyl)-N'-(3-ethylphenyl)-N'-methyl guanidine.HCl (CDD-251A)

N-(8-quinolinyl)-N'-(3 -ethyphenyl)-N'-methyl guanidine.HCl was prepared from N-(8-quinolinyl) amine.HCl and N-methyl, N-(3-ethylphenyl) cyanamide following the general catalytic process described above. Analytical data for the guanidine hydrochloride product are as follows:

Recrystallized from absolute ethanol/ether acetate; white solid: m.p. 145° C. (dec); $^1$H NMR (300 MHz, CD$_3$OD) δ8.98–8.99 (d, J=3 Hz, 1, Ar—H), 8.50–8.52 (d, J=8 Hz, 1, Ar—H), 7.97–7.99 (d, J =8 Hz, 1, Ar—H), 7.24–7.78 (m, 7, Ar—H), 3.57 (s, 3, N'—CH$_3$), 2.64–2.72 (q, J=7.5 Hz, 2, CH$_2$), 1.20–1.25 (t, J=7.5 Hz, 3, CH$_3$); MS (El); m/e 304 (M$^+$ for free base); Anal. (C$_{19}$H$_{20}$N$_4$. HCl) Calcd (%): C 66.95, H 6.21, N 11.82. Found (%): C 67.21, H 6.28, N 11.66.

EXAMPLE 4

Synthesis of N-(5-isoquinolinyl)-N'-(3-ethylphenyl) -N'-methyl guanidine.HCl (CDD-2518A)

N-(5-isoquinolinyl)-N'-(3-ethylphenyl)-N'-methyl guanidine.HCl was prepared from N-(5-isoquinolinyl) amine.HCl and N-methyl, N-(3-ethylphenyl) cyanamide following the general catalytic process described above. Analytical data for the guanidine hydrochloride product are as follows:

Recrystallized from absolute ethanol/ether acetate; Brown solid: m.p. 220° C.; $^1$H NMR (300 MHz, CD$_3$OD) δ9.92 (s, 1, Ar—H), 8.72 (s, 1, Ar—H), 8.57–8.60 (m, 2, Ar—H), 8.27–8.30 (d, J=7 Hz, Ar—H), 8.09–7.14 (t, J=7 Hz, 1, Ar—H), 7.42–7.46 (m, 2, Ar—H), 7.30–8.32 (d, J=7 Hz, 1, Ar—H), 3.60 (s, 3, N'—CH$_3$), 2.69–2.76 (q, J=7.5 Hz, 2, CH$_2$), 1.25–1.30 (t, J=7.5 Hz, 3, CH$_3$); MS (El); m/e 304 (M$^+$for free base).

EXAMPLE 5

N-(1-naphthyl)-N'-(2-pyridyl)-N-methyl guanidine.HCl (CDD-2519A)

N-(1-naphthyl)-N'-(2-pyridyl)-N-methyl guanidine.HCl was prepared from N-(2-pyridyl) amine.HCl and N-(1-naphthyl) -N-methyl cyanamide following the general catalytic process described above. Analytical data for the guanidine hydrochloride product are as follows:

Recrystallized from absolute ethanol/ether acetate; white solid: m.p. 179° C.; $^1$H NMR (300 MHz, CD$_3$OD) δ8.33–8.40 (m, 1, Ar—H), 8.06–8.14 (m, 2, Ar—H), 7.86–7.93 (m, 1, Ar—H), 7.62–7.70 (mz, 5, Ar—H), 7.20–7-30 (br s, 1, Ar—H, 3.62–3.68 (br s, 3, N—CH$_3$); MS (El); m/e 276 (M$^{30}$ for free base).

EXAMPLE 6

Synthesis of N-(1-naphthyl)-N'-benzyl-N'-methyl guanidine.HCl (CDD-2520A)

N-(1-naphthyl) -N'-(benzyl)-N'-methyl guanidine.HCl was prepared from N-(1-naphthyl) amine.HCl and N-methyl, N-benzyl cyanamide following the general catalytic process described above. Analytical data for the guanidine hydrochloride product are as follows:

Recrystallized from absolute ethanol/ether; white solid: m.p. 176° C.; $^1$H NMR (300 MHz, CD$_3$OD) δ8.00–8.05 (d, J=8 Hz, 1, Ar—H), 7.77–7.84 (d, J=8 Hz, 1, Ar—H), 7.35–7.65 (m, 10, Ar—H); 4.85 (s, 2, benzyl), 3.25 (s, 3, N'—CH$_3$); MS (El); m/e 298 (M$^+$ for free base).

EXAMPLE 7

N-(3-ethylphenyl)-N'-(benzyl)-N,N'-dimethyl guanidine.HCl (CDD-2521A)

N-(3-ethylphenyl)-N'-(benzyl)-N,N'-dimethyl guanidine.HCl was prepared from N-methyl, N-benzyl amine.HCl and N-methyl, N-benzyl cyanamide following the general catalytic process described above. Analytical data for the guanidine hydrochloride product are as follows:

Recrystallized from absolute ethanol/ether; white solid: m.p. 180° C. (dec); $^1$H NMR (300 MHz, CD$_3$OD) δ7.00–7.46 (m, 8, Ar—H); 4.40 (s, 2, benzyl), 3.45 (s, 3, N—CH$_3$), 2.67 (s, 3, N'—CH$_3$), 2.56–2.63 (q, J=7.5 Hz, 2, CH$_2$), 1.18–1.23 (t, J=7.5 Hz, 3, CH$_3$); MS (El); m/e 281 (M$^+$ for free base).

EXAMPLE 8

Synthesis of N-(1-naphthyl)-N'-(3-ethylphenyl)-N'-methyl guanidine (CDD-515A)

N-(1-naphthyl)-N'-(3-ethylphenyl)-N'-methyl guanidine.HCl was also prepared from N-(1-naphthyl) amine.HCl and N-methyl, N-(3-ethylphenyl) cyanamide by the procedure set forth below. Note that in this example the aluminum chloride catalyst was provided in a single addition, as compared with the batchwise addition in Example 1.

To a stirred solution of 6.346 g (39.66 mmol) N-methyl, N-(3-ethylphenyl) cyanamide in 120 ml chlorobenzene at room temperature under argon atmosphere was quickly added 5.817 g (43.63 mmol) anhydrous $AlCl_3$ (production of fumes with color change from clear orange to red-black slurry). Note that it may be more convenient to do the reverse addition: i.e., weigh the $AlCl_3$ first and then to this, add a solution of the cyanamide in chlorobenzene. After stirring for 5 min, 7.120 g (39.66 mmol) of freshly prepared naphthylamine.HCl was added and the reaction mixture was heated to reflux on an oil bath for 10 hr. A water cooled condenser was used with the oil bath temperature being kept at around 150° C. and argon atmosphere being maintained throughout the experiment. The mixture was then allowed to cool to room temperature. TLC of the reaction mixture at this point showed complete disappearance of the cyanamide and only a very faint spot corresponding to the amine.

Approximately 50 ml ethanol was then added to reaction mixture and the resulting solution was concentrated on Rotavapor. Ethanol was added to facilitate the removal of chlorobenzene by forming a lower boiling azeotropic mixture. The concentrated product mixture was chromatographed on a flash column (silica gel: 60–200 mesh, 50× w/w; eluent: initially 100% EtOAc followed by 15–20% MeOH in EtOAc; the desired product coming out of the column had a pinkish color). It is preferred that any leftover chlorobenzene and nonpolar impurities be removed by flash column using 100% ethyl acetate. This greatly facilitates the isolation of essentially pure product at a later stage by elution with methanol/ethyl acetate, since the subsequent step of recrystallization is much easier to perform on this chromatographed material. All the fractions containing the desired product were combined and concentrated under reduced pressure to afford 12.3 g (91.6%) of a pinkish sticky solid. The chromatographed material, which was shown to be practically pure by 1H NMR analysis, was taken up in hot ethanol (50–60 ml), treated with decolorizing charcoal (0.5 g) and filtered through Celite. The filtrate was concentrated down to an oil and then recrystallized by slow diffusion of ether (an EtOH/EtOAc combination also worked in some cases) to furnish white-colorless crystals. Yield: 10.8 g (80.2%).

Analytical data for the guanidine hydrochloride product are as follows:

m.p. 221° C. (a second recrystallization improved the m.p. to 225° C.); MS (EI): m/e 303.25.

Anal. ($C_{20}H_{21}N_3$.HCl) Calcd (%): C 70.68, H 6.53, N 12.36. Found (%): C 70.67, H 6.49, N 12.36.

EXAMPLE 9

Synthesis of N-(5-quinolinyl)-N'-(3-ethylphenyl)-N'-methyl guanidine.HCl

N-(5-quinolinyl)-N'-(3-ethylphenyl)-N'-methyl guanidine.HCl was prepared from 5-amino quinoline.CHl and N-methyl, methyl, N-(3-ethylphenyl) cyanamide with aluminum chloride catalyst by refluxing in chlorobenzene for 5 hr. The work-up of the reaction was similar to the one described in Example 8.

Recrystallized from absolute ethanol/ether, yellow solid; m.p. 238° C.; MS (EI) m/e 304 ($M^+$ for free base).

EXAMPLE 10

Synthesis of N-(1-naphthyl)-N'-(3-ethylphenyl)-N'-methyl guanidine (CDD-2515A)

A. Procedure for the preparation of N-methyl-3-ethyl aniline hydrochloride

Step 1: Formation of N-(3-ethyl-phenyl) formamide

A mixture of 36.4 g (300 mmol) 3-ethyl aniline and 19.5 ml (420 mmol) of formic acid (95–97%) was heated at 100°–105° C. for a period of 2.5 hr. After cooling to ambient temperature, the reaction mixture was diluted with 200 ml of dichloromethane and then washed successively with saturated sodium bicarbonate and brine. The organic layer was dried over $Na_2SO_4$ and concentrated in vacuo to afford 42.2 g (95% yield) of the crude formamide, which could be used as such in the next step.

Step 2: Reduction of N-(3-ethylphenyl) formamide to N-methyl-3-ethylaniline

The formamide obtained in the above step was dissolved in 250 ml anhydrous tetrahydrofuran (THF) under nitrogen atmosphere in a 3-necked flask fitted with a mechanical stirrer. After cooling the flask in ice-bath, a total of 13.6 g (340 mmol, 1.2 mole equivalent) of lithium aluminum hydride (95%) was added in a batchwise fashion to the formamide over a period of 40 min to avoid an exothermic reaction. After completion of the addition the reaction was allowed to stir at ambient temperature overnight over a period of 12 hr. The excess hydride was then carefully destroyed by slow addition of a saturated solution of $Na_2SO_4$ to the cooled reaction mixture accompanied by vigorous stirring. The resultant white solid was filtered off, washed with THF and the combined filtrate was concentrated to afford a crude liquid, which was distilled under reduced pressure (using short-path distillation) to afford 32.2 g (84% yield) of N-methyl-3-ethyl aniline as a colorless liquid.

Step 3: Preparation of N-methyl-3-ethyl aniline. hydrochloride

The N-methyl-3-ethyl aniline obtained in the previous step was dissolved in 250 ml anhydrous ether and to this was added (by annulation) about 400 ml of HCl (1.0M solution in ether) at ambient temperature. The resultant white precipitate was filtered through a Buchner funnel, washed with ether, and dried to afford 39.0 g (95% yield, 76% overall in 3 steps from 3-ethyl aniline) of a white solid.

B. Procedure for the preparation of 1-naphthyl cyanamide:

To 40 g (280 mmol) 1-naphthylamine dissolved in ether at r.t. was added by cannulation a solution of 35 ml (175 mmol) BrCN in CH3CN while stirred (mechanical stirring preferred) and cooled with cold water. Note that this was an exothermic reaction. A crystalline precipitate of amine.HBr was formed rapidly. After 23 hours, the precipitate was filtered off with suction and washed with generous amounts of ethyl acetate to recover 30.1 g (134 mmol) of the naphthylamine.HBr. The filtrate was concentrated on Rotavapor to leave 25.1 g of purple colored solid of the crude cyanamide, whose TLC (eluent: 25% ethyl acetate in hexanes) showed the presence of minor amounts of amine or amine.HBr. This was redissolved in ethyl acetate and washed successively with 5% (v/v) cold aq. HCl, water and brine. Drying the organic layer over anhydrous $Na_2SO_4$ and solvent removal in vacuo furnished 22.0 g (136 mmol, 97.1% yield based on the theoretical yield of 140 mmol) of practically pure 1-naphthyl cyanamide as a pink solid which could be used as such in the subsequent step.

The naphthylcyanamide was purified for analytical purposes by recrystallization from warm chloroform/cold hexanes. More specifically, 3.0 g of the naphthylcyanamide was dissolved in warm chloroform and to this was added hexanes dropwise with stirring to obtain a milky solution. The milky solution was cooled further to obtain the naphthylcyanamide as a pinkish-white solid, which was isolated by suction filtration (2.3 g). Alternatively, the crude naphthylcyanamide was recrystallized by the following procedure: 1.0 g of crude naphthylcyanamide was dissolved in about 3 ml of warm methanol and to this was added water dropwise till a milky solution was obtained; the milky solution was left overnight and then filtered and dried to obtain 0.85 g of the naphthylcyanamide as mostly white solid.

C. Procedure for the preparation Of CDD-2515A

A mixture of 20.0 g (119 mmol) 1-naphthyl cyanamide and 19.4 g (113 mmol) amine.HCl thus prepared was heated in 100 ml chlorobenzene to reflux (oil bath temp. 140° C) for 25 hr. (Magnetic stir bar was used for stirring, although mechanical stirring is preferred to decrease the reaction time.) At this juncture, TLC showed complete conversion of the cyanamide with minor amount of amine.HCl. After cooling to ambient temperature, excess ether was added to the reaction mixture which resulted in precipitation of a dark pink solid. This was filtered through a Buchner funnel and washed several times with ethyl acetate in order to remove colore impurities.

The residue was taken up in boiling ethanol, treated with Norit (decolorizing charcoal) for 0.5 hr and then filtered through a medium porosity filter funnel. The filtrate was concentrated to obtain a solid which on recrystallization from ethanol/ethyl acetate afforded 27.9 g (72.7%, first crop) of white solid with a pinkish tinge. Concentration of the mother liquor gave 3.1 g (8.1%, second crop) of additional CDD-2515A as a pinkish-white solid. Total yield 31.0 g (80.8%).

Analytical data for the guanidine hydrochloride product are as follows:

Anal. ($C_{20}H_{21}N_3$.HCl) Calcd (%): C 70.68; H 6.53; N 12.36. Found: C 70.64; H 6.30; N 12.36 (first crop); C 70.49; H, 6.79; N, 12.46 (second crop).

EXAMPLE 11

Synthesis of N-(1-naphthyl)-N'-(3-chlorophenyl)-N'-methyl guanidine.HCl

N-(1-Naphthyl)-N'-(3-chlorophenyl)-N'-methyl guanidine.HCl was prepared from 1-naphthyl cyanamide and N-methyl-3chloro aniline.HCl in 76% yield by refluxing in toluene for 4 hr. The work-up of the reaction was similar to the one described in Example 10.C.

Recrystallized from absolute ethanol/ether, white solid; m.p. 126° C.; MS (El) m/e 309 ($M^+$ for free base).

EXAMPLE 12

Synthesis of N-(1-naphthyl)-N'-(3-fluorophenyl)-N'-methyl guanidine.HCl

N-(1-naphthyl)-N'-(3-fluorophenyl)-N'-methyl guanidine.HCl was prepared from 1-naphthyl cyanamide and N- methyl-3-flouoro aniline.HCl in 69% yield by refluxing in toluene for 4 hr. The work-up of the reaction was similar to the one described in Example 10.C.

Recrystallized from absolute ethanol/ether, white solid, m.p. 146° ; MS (El) m/e 293 ($M^+$ for free base).

EXAMPLE 13

Synthesis of N-(1-naphthyl)-N'-(3-bromophenyl)-N'-methyl guanidine.HCl

N-(1-naphthyl)-N'-(3-bromophenyl)-N'-methyl guanidine.HCl was prepared from 1-naphthyl cyanamide and N-methyl-3-bromo aniline.HCl by the method similar to the one described in Example 10.C.

Recrystallized from absolute ethanol/ether, white solid, m.p. 162° ; MS (El) m/e 354 ($M^+$ for free base).

EXAMPLE 14

Synthesis of N-(1-naphthyl)-N'-(3-iodophenyl)-N'-methyl guanidine.HCl

N-(1-naphthyl)-N'-(3-iodophenyl)-N'-methyl guanidine.HCl was prepared from 1-naphthyl cyanamide and N-methyl-3-iodo aniline.HCl by the method similar to the one described in Example 10.C.

Recrystallized from absolute ethanol/ether, white solid, m.p. 174° ; MS (El) m/e 401 ($M^+$ for free base). EXAMPLE 15

Synthesis of N-(1-naphthyl)-N'-(3-methoxyphenyl)-N'-methyl guanidine.HCl

N-(1-naphthyl)-N'-(3-methoxyphenyl)-N'-methyl guanidine.HCl was prepared from 1-naphthyl cyanamide and N-methyl-3-methoxy aniline.HCl by the method similar to the one described in Example 10.C.

Recrystallized from absolute ethanol/ether, white solid, m.p. 124° ; MS (El) m/e 305 ($M^+$ for free base).

The preceding examples can be repeated with similar success by substituting the generically or specifically described reactants and/or operating conditions of this invention for those used in these examples. For instance, a lower boiling solvent, e.g., toluene, may be used instead of the higher boiling chlorobenzene in both the catalytic process and the non-catalytic process for preparing substituted guanidines. The time for completion of the reaction varies, e.g., from 2 hours to 24 hours, depending on the reactivity of the amine and the cyanamide used in the reaction.

From the foregoing description, one skilled in the art can easily ascertain the essential characteristics of this invention, and without departing from the spirit and scope thereof, can make various changes and modifications of the invention to adapt it to various usages and conditions. Thus, other embodiments are also within the claims.

What is claimed is:

1. A process for the preparation of N-(1-naphthyl)-N'-(3-ethylphenyl)-N'-methyl guanidine which comprises the step of reacting a mono-substituted cyanamide $R^1NH$—CN with a di-substitute amine $R^2NHR^3$, wherein said mono-substituted cyanamide is N-(1-naphthyl)cyanamide and said di-substituted amine is N-methyl-N-(3-ethylphenyl) amine.

2. The process of claim 1, wherein said reacting step is performed by refluxing said substituted cyanamide and said substituted amine in a boiling solvent.

* * * * *

UNITED STATES PATENT AND TRADEMARK OFFICE
CERTIFICATE OF CORRECTION

PATENT NO. : 5,489,709
DATED : February 6, 1996
INVENTOR(S) : Graham J. Durant, et al It is certified that error appears in the above-indentified patent and that said Letters Patent is hereby corrected as shown below:

Col. 2, line 39, "$C_2C_8$" should be --$C_2$-$C_8$--.

Col. 2, line 50, "$R^3NH$-$R^4$" should be --$R^3$-$NH$-$R^4$--.

Col. 3, line 2, after ".", delete "More".

Col. 3, line 28, "$C_1 14C_5$" should be --$C_1$-$C_5$--.

Col. 3, line 32, "$C_1$ -$C_5$" should be --$C_1$-$C_5$--

Col. 3, line 67, "$TICl_4$" should be --$TiCl_4$--.

Col. 4, line 35, "4-bromo-3methyl" should be --4-bromo-3-methyl--.

Col. 4, line 45, "piperizinyl" should be --piperazinyl--.

Equation (II) should read as shown below:

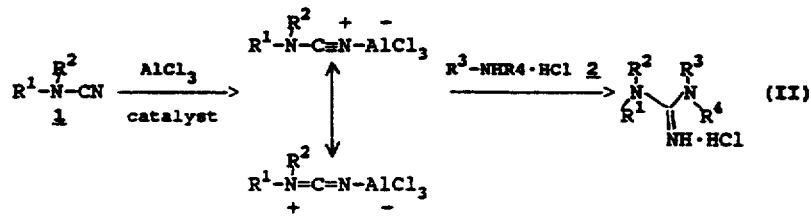

UNITED STATES PATENT AND TRADEMARK OFFICE
CERTIFICATE OF CORRECTION

PATENT NO. : 5,489,709
DATED : February 6, 1996
INVENTOR(S) : Graham J. Durant, et al It is certified that error appears in the above-indentified patent and that said Letters Patent is hereby corrected as shown below:

Col. 5, line 26, "1" should be --$\underline{1}$--.

Col. 5, line 27, "2" should be --$\underline{2}$--.

Equation (III) should read as shown below:

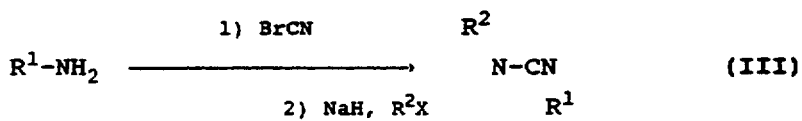

$$R^1-NH_2 \xrightarrow[\text{2) NaH, } R^2X]{\text{1) BrCN}} \underset{R^1}{\overset{R^2}{N-CN}} \quad\quad (III)$$

$$\underline{1}$$

Col. 5, line 41, "2" should be --$\underline{2}$--.

Examples 2 and 3, should read as shown below:

Table I

| Example | Starting Amine | Starting Cyanamide | Product | M. P. | % yield |
|---|---|---|---|---|---|
| 2 | [structure] | [structure] | CDD-2516A | 128°C | 74% |
| 3 | [structure] | [structure] | CDD-2517A | 145°C (dec) | 31% |

UNITED STATES PATENT AND TRADEMARK OFFICE
CERTIFICATE OF CORRECTION

PATENT NO. : 5,489,709
DATED : February 6, 1996
INVENTOR(S) : Graham J. Durant, et al It is certified that error appears in the above-indentified patent and that said Letters Patent is hereby corrected as shown below:

Col. 8, line 61, "Examples" should be --Example--.

Col. 9, line 19, after "2515A", insert --)--.

Col. 9, line 50, "6 669" should be --6.669--.

Col. 9, line 50, "12 00" should be --12.00--.

Col. 9, line 55, "251A" should be --2517A--.

Col. 10, line 37, "M$^{30}$" should be --M$^+$--.

Col. 11, line 2, "515A" should be --2515A--.

Col. 11, line 45, "1H" should be --$^1$H--.

Col. 11, line 66, after "N-methyl," delete "methyl,".

Col. 12, line 54, "CH3CN" should be --CH$_3$CN--.

Col. 13, line 18, "Of" should be --of--.

UNITED STATES PATENT AND TRADEMARK OFFICE
CERTIFICATE OF CORRECTION

PATENT NO. : 5,489,709
DATED : February 6, 1996
INVENTOR(S) : Graham J. Durant, et al It is certified that error appears in the above-indentified patent and that said Letters Patent is hereby corrected as shown below:

Col. 13, line 30, "colore" should be --color--.

Col. 13, line 63, "flouoro" should be --fluoro--.

Col. 14, line 26, start a new section with "EXAMPLE 15".

Col. 14, line 56, "di-substitute" should be --di-substituted--.

Signed and Sealed this

Twenty-fifth Day of June, 1996

Attest:

BRUCE LEHMAN

*Attesting Officer*    *Commissioner of Patents and Trademarks*